United States Patent [19]

Fulton, Jr.

[11] Patent Number: 5,705,179
[45] Date of Patent: Jan. 6, 1998

[54] TISSUE AUGMENTATION WITH PERFLUOROPOLYETHER COMPOUNDS

[75] Inventor: James E. Fulton, Jr., Newport Beach, Calif.

[73] Assignee: Vivante Internatinale, Inc., Boca Raton, Fla.

[21] Appl. No.: 195,189

[22] Filed: Feb. 10, 1994

[51] Int. Cl.⁶ .................... A61F 2/02; A61F 2/08
[52] U.S. Cl. .................. 424/423; 623/13; 623/14
[58] Field of Search ................ 424/423; 623/13, 623/14

[56] References Cited

U.S. PATENT DOCUMENTS

| | | |
|---|---|---|
| 4,189,501 | 2/1980 | Fulton, Jr. . |
| 4,803,067 | 2/1989 | Brunetta et al. . |
| 4,959,171 | 9/1990 | Pantini et al. . |
| 5,043,356 | 8/1991 | Fulton, Jr. . |
| 5,093,023 | 3/1992 | Pantini et al. . |
| 5,439,673 | 8/1995 | Murray ............... 424/70.12 |

*Primary Examiner*—Carlos A. Azpuru
*Attorney, Agent, or Firm*—Knobbe Martens Olson & Bear, LLP

[57] ABSTRACT

Perfluoropolyether compounds are used for augmenting lost or damaged tissue. The perfluoropolyether compounds are subcutaneously administered in the form of micro-droplets to stimulate the formation of collagen at selected sites of tissue loss or damage in an individual in need thereof.

18 Claims, No Drawings

TISSUE AUGMENTATION WITH PERFLUOROPOLYETHER COMPOUNDS

FIELD OF THE INVENTION

The present invention relates to chemically non-reactive, liquid perfluoropolyether compounds and the use of such compounds for augmenting tissue lost or damaged as a result of, for example, birth defects, lacerations, soft tissue traumas and diseases such as acne.

BACKGROUND OF THE INVENTION

For the past century, physicians have attempted to augment tissue, which has been lost through trauma or disease. Typically, such augmentation is accomplished by the injection of or stimulation of collagen production. Collagen is an insoluble fibrous protein that occurs in vertebrates as the chief constituent of the fibrils of connective tissue, such as that found in skin and tendons.

In the past, surgery has been utilized to collect fat or tendon from a donor site of a patient, followed by its insertion into the site lacking collagen. However, during such extensive surgery, trauma causes an inflammatory response which can result in the loss of augmenting material. Therefore, such surgical techniques have been less than optimal.

Over the last fifteen years, liquid collagen has become available from bovine sources. It has been commonly used to fill acne scars. However, collagen from bovine sources can cause severe allergic reaction in, for example, about 1–3% of patients. Moreover, bovine collagen is largely resolved over a 3–6 month period in humans. Although repeated injections of bovine collagen can be used in certain patients, bovine collagen is expensive and is believed to be relatively ineffective.

More recently, sources of fibrin have become available. Fibrin is a white insoluble fibrous protein that is essential to the clotting of blood which is formed from fibrinogen by the action of the proteolytic enzyme, thrombin. A patient's own blood is mixed with a fibrin composition and injected into the site to be augmented. Such injections, however, irritate the skin, causing the formation of new collagen by the inflammatory response. Moreover, the fibrin is rapidly re-absorbed and the augmentation quickly diminishes. As with the injection of liquid bovine collagen, injections of fibrin mixtures are very expensive and are also believed to be ineffective.

Liquid silicone has also been used in methods of inducing tissue augmentation. Liquid silicone, manufactured under the trade name, Dow Fluid 200, by Dow Chemical, Midland, Mich., has been used for the last thirty years as an inert substance to fill depressed valleys of ache scars or traumatic areas of tissue loss. Commonly, micro-droplets are injected through a small needle, such as a 27 or 30 gauge needle, approximately every thirty days to cause augmentation of the acne scars or traumatic areas. Unfortunately, if the micro-droplet technique is not used properly and too much silicone is injected into one site, tissue granulomas may develop causing persistent red nodules. To reduce the induced inflammation, injections with anti-inflammatory hydrocortisone are administered. Even though silicone has been somewhat successful, it has not been approved by the Food and Drug Administration in the United States for tissue augmentation, and it is virtually unavailable at present to physicians for medical use.

More recently, a solid organic molecule that is surrounded by inorganic fluoride, tetrafluoropolyethylene, has been used under the trade name Gor-Tex and manufactured by Gore, Inc., Flagstaff, Ariz. Large sheets of the Gor-Tex material are used to repair hernias in older individuals with weakened muscle and tissue structure. Gor-Tex Suture® has also become available as a non-reactive suture substance. These permanent sutures and strips of Gor-Tex material are currently being used to augment tissue but have the disadvantage of being solid materials which do not provide the versatility of liquid material. Other disadvantages of using Gor-Tex are, for example, shifting of the solid material in the soft tissue and the tendency of the human body to reject implants.

Consequently, the foregoing disadvantages demonstrate that there is a need for an inexpensive, effective and safe treatment for augmenting tissue loss or damage due to, for example, birth defects, lacerations, soft tissue and traumas or diseased areas of tissue in humans.

SUMMARY OF THE INVENTION

In brief, the present invention alleviates and overcomes certain of the above-referenced problems and shortcomings of the present state of the art through the discovery of pharmaceutical compositions and uses thereof for stimulating collagen formation to augment tissue, e.g., dermal, subcutaneous, muscular or bone tissue, which has been lost or damaged due to, for instance, traumas, lacerations, birth defects or disease, such as ache. The pharmaceutical compositions of the present invention are comprised of at least an effective amount of a liquid, inert perfluoropolyether, such as a perfluoropolyethylisopropylether, and are administered preferably as micro-droplets by, for instance, subcutaneous injections at predetermined sites. The liquid perfluoropolyethers of the present invention have molecular weights which are similar to silicone and are believed to be equal or superior to silicone injections for tissue augmentation.

It has been surprisingly discovered that the pharmaceutical compositions of the present invention are non-sensitizing and non-irritating. Moreover no side effects, such as persistent red nodules, or allergic reactions, have been observed to date with the novel pharmaceuticals of the present invention. In addition, microscopic examination has surprisingly revealed that there is a significant stimulus in new collagen formation at the sites of injection with the pharmaceutical compositions of the present invention. Quite amazingly and unexpectedly, the augmentation induced by treatment with the pharmaceutical compositions of the present invention has been found to be more permanent than when tissue is augmented with the treatments available heretofore.

The present invention therefore provides an effective and long sought solution to augmenting tissue that has been lost or damaged due to, for example, soft tissue, lacerations, birth defects, and diseases like acne.

The above features and advantages of the present invention will be better understood with reference to the following Detailed Description and Examples which are illustrative of the present invention.

DETAILED DESCRIPTION

By way of illustrating and providing a more complete appreciation of the present invention and many of the attendant advantages thereof, the following Detailed Description is given concerning the pharmaceutical compositions and methods for augmenting tissue, such as dermal, subcutaneous, muscular or bone tissue, that has been lost or damaged as a result of, for example, soft tissue, lacerations, and birth defects, and diseases like ache. The pharmaceutical compositions of the present invention are comprised of liquid, inert perfluoropolyether compounds, such as perfluoropolyethylisopropyl ether.

In the context of this disclosure, the following terms shall be defined as follows unless otherwise stated. By the terms "augmentation," "augment(ed)" or "augmenting," they are used broadly herein and mean filling in tissue, such as dermal, subcutaneous, bone or muscular tissue that has been lost or damaged.

By the term "tissue," it too is used broadly herein and refers to, for instance, subcutaneous, dermal, bone and muscular tissue. Dermal tissue refers to, for example, papillary or reticular dermis and adjacent tissue including fibrous, fatty subcutaneous sections of human tissue.

By the term "an effective amount," it also is used herein in a broad sense and refers to an amount sufficient to produce the desired augmentation of lost or damaged tissue in selected areas of administration, such as about 0.05 ml to about 0.2 ml and preferably about 0.1 ml of total volume of a perfluoropolyether per site.

By the term "micro-droplet(s)," it too is used herein in a broad sense and refers to small droplets of a perfluoropolyether delivered through, for example, a 27 or 30 gauge needle.

By the term "perfluoropolyether(s)," it is also used in a broad sense and is meant to refer to inert, perfluorinated liquid compounds having a very high concentration of "organic fluorine," but being virtually if not totally free of flourine and inorganic fluorides, that are capable of augmenting dermal tissue. Included in such compounds are those referred to as perfluoropolyether or perfluorinated polyethers or polyoxyperfluoroalkanes or perfluoropolyothylisopropyl ether.

More particularly, the perfluoropolyethers utilizable as neat liquids or in the compositions in accordance with the present invention are compounds which contain perfluoroalkylene oxide units or perfluoroxetane rings.

In particular, the repeating units are chosen from the following:

(a) $C_2F_4O$ and $CF_2O$ statistically distributed along the chain;

(b) $C_2F_4O$, $C_3F_6O$ and CFXO (X=F or $CF_3$) statistically distributed along the chain;

(c) $C_3F_6O$ and CFXO (X=F or $CF_3$) statistically distributed along the chain;

(d) oxetane rings:

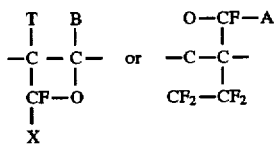

in which A, T and X are equal to or different from each other, are perfluorooxyalkyl, perfluoropolyoxyalkyl or perfluoroalkyl radicals.

The end groups of the perfluoropolyethers may be like or unlike each other and are selected in particular from the radicals F, $CF_3$, $C_2F_5$, $C_3F_7$, Br, or from polar groups containing one or more electron donor atoms or from groups containing one or more aromatic rings, either or not containing heteroatoms, capable of giving rise to coordinated bonds or charge-transfer bonds.

The mean number average molecular weight is generally higher than 500 and ranges in particular from 1,000 to 10,000. The viscosity values (cSt at 20° C.) are generally in the range of from 30 to 5,000.

Examples of perfluoropolyethers are:

$$CF_3O\text{—}(C_3F_6O)_m\text{—}(CFXO)_n\text{—}CF_2Y \qquad (I)$$

in which X and Y are a radical F or $CF_3$ and m and n are integers, the m/n ratio ranging from about 5 to about 40. These compounds and the method of preparing them are described in British Pat. No. 1,104,482 which is incorporated herein by reference in its entirety.

$$C_3F_7O\text{—}(C_3F_6O)_m\text{—}Rf \qquad (II)$$

in which Rf may be $C_2F_5$, $C_3F_7$, $CFHCF_3$, m is an integer higher than about 2, preferably from about 10 to about 100. These compounds and the method of preparing them are described in the U.S. Pat. No. 3,242,218 which is likewise incorporated herein by reference in its entirety.

$$CF_3O(C_3F_6O)_m(C_2F_4O)_n(CFXO)_q\text{—}CF_3 \qquad (III)$$

where X=F, $CF_3$ and m, n and q are integers; m+n+q= 10–300; n/q=0.5–5; m/q+n=0.01–0.4. These compounds and the method of preparing them are described in U.S. Pat. No. 3,665,041 which is incorporated herein by reference in its entirety.

$$CF_3O(C_2F_4O)_p(CF_2O)_q\text{—}CF_3 \qquad (IV)$$

where p and q are integers alike or different from each other and the p/q ratio ranges from about 0.5 to about 1.5. Examples of these compounds and the method of preparing them are described in U.S. Pat. Nos. 3,715,378 and 3,665, 041 which are incorporated herein by reference in their entireties. Examples of perfluoropolyethers containing polar end groups are described in U.S. Pat. No. 3,847,978 and in Italian Patent Application Nos. 21480 A/84 and 21481 A/84 which also are incorporated herein by reference in their entireties.

(V) The compounds having the oxetane structure are described in Italian Patent Application No. 19496 A/85 which is incorporated herein by reference in its entirety.

(VI) Perfluoropolyethers comprising $CF_2CF_2CF_2O$ units.

(VII) Perfluoropolyethers comprising $CF_2CF_2O$ units.

The perfluoropolyethers comprising $CF_2CF_2O$ units or $CF_2CF_2CF_2O$ units are prepared respectively according to EP published application No. 148,482 (Daikin) and U.S. Pat. No. 4,523,039 (Lagow) which are incorporated herein by reference in their entireties.

(VIII) In addition to the neutral perfluoropolyethers indicated above, one may also use perfluoropolyethers with functionalized end groups, such as those described, for example, in European patent application Nos. 165,649 and 165,650, U.S. Pat. No. 3,810,874, EP No. 148,482 (Daikin), EP No. 151,877 (3M) or in an Italian application No. 22929 A/85, which are incorporated herein by reference in their entireties.

Preferred liquid perfluoropolyethers of the present invention are perfluoroethylisopropyl ether and have the following chemical structures:

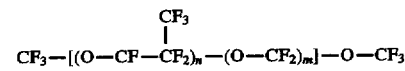

where n/m=about 20+ about 40. These compounds are generally manufactured by Ausimont of Milan, Italy and sold under the name Fomblin HC. Such compounds are disclosed in U.S. Pat. No. 4,803,067, No. 4,959,171 and No. 5,093,023. It should therefore be understood that U.S. Pat. No. 4,803,067, No. 4,959,171 and No. 5,093,023 are incorporated herein by reference in their entirety. Exemplary of such Fomblin HC compounds include Fomblin HC/04, average molecular weight 1500, Fomblin HC/25, average molecular weight 3200 and Fomblin HC/R, average molecular weight 6250. It should be appreciated that different viscosities and, to some extent, differences in other physical and chemical properties correspond to the different molecular weights. More particularly, see Table I.

TABLE I

| Property (Typical Value) | HC/04 | HC/25 | HC/R | Method |
|---|---|---|---|---|
| Average molecular weight | 1500 | 3200 | 6250 | PF 29/24 |
| Kinematic viscosity at 20° C. (cSt) | 40 | 250 | 1300 | ASTM D445 |
| Pour point (°C.) | −62 | −35 | −25 | ASTM D 97 |
| Vapor tension (mm Hg) | $10^{-3}$ | $10^{-5}$ | $10^{-7}$ | |
| Evaporation loss (1 hr at 105° C. g/100 g) | 0.5 | 0.05 | 0.02 | ASTM D972 |
| Neutralization no. (mg KOH/g) | 0.02 | 0.02 | 0.02 | PF 29/48 |
| Interfacial tension against water (at 20° C., dynes/cm) | 55 | 55 | 55 | PF 29/5 |
| Surface tension (at 20° C. dynes/cm) | 21 | 22 | 24 | |
| Refractive index | 1.293 | 1.299 | 1.302 | PF 29/3 |
| Density (g/cm³) | 1.87 | 1.90 | 1.91 | ASTM D891/A |

Fomblin HC fluids are generally insoluble in common ingredients used in, for example, the cosmetic and/or pharmaceutical industry. Nevertheless, Fomblin HC fluids vary from partially soluble to completely miscibile with fluoro-compounds, according to their molecular weights and to the fluorine content of the latter. See Table II.

TABLE II

| Compound/Fomblin Grade | HC/04 | HC/25 | HC/R |
|---|---|---|---|
| Water | I | I | I |
| Ethanol | I | I | I |
| Glycerin | I/D | I/D | I/D |
| Glycerin (plus 5% water) | I/D | I/D | I/D |
| Diglycerin | I/D | I/D | I/D |
| Acetone | I | I | I |
| Polyethylene Glycol | I | I | I |
| Sorbeth-30 | I | I | I |
| Glyceryl Mono Distearate | I | I | I |
| Caprilic/Capric Triglyceride | I | I | I |
| Sodium Lauryl Ether Sulfate | I | I | I |
| Mineral Oil | I | I | I |
| Dimethicone | I | I | I |
| HCFC-124 | S | S | S |
| HFC-134 a | S | S | SW |
| Trichloro-trifluoroethane | M | M | M |
| Perfluoro-octane | M | M | M |

Key:
I: insoluble (less than 10 ppm soluble)
D: dispersible
S: soluble (more than 10% soluble)
SW: soluble warm (more than 5% soluble at 20° C.)
M: miscible A most preferred perfluoropolyether for augmenting lost or damaged tissue in accordance with the present invention is Fomblin HC fluids and in particular Fomblin HC/R. This perfluoropolyether, as other perfluoropolyethers of the present invention, may be obtained from Ausimont of Milan, Italy or by the photo-oxidation of hexafluorapropene at low temperature. This process yields-linear polymers that have a random distribution of oxyhexafluoropropene units and oxydifluoromethylene units, with a much larger proportion of the former and minor amounts of the latter, linked through ether bonds. Moreover, the absence of hydrogen atoms in the structure, the presence of strong covalent bonds such as C—O and C—F, the chain ending with perfluoroalkyl groups, ensure excellent chemical and thermal stability, with other useful physical properties due to the extreme flexibility of the perfluorinated polyether backbone and to the very high content of fluorine atoms (around 70%). Unlike hydrocarbons which become waxes and solids, perfluoropolyethers are liquid even at very low temperatures and beyond chain lengths of about 14 carbons.

The Fomblin HC fluids have a unique combination of properties. They are completely chemically and biologically inert. They have low surface tensions, are thermally stable and have average molecular weights of about 1500, 7200 and 6250. See Table I. Moreover, they are insoluble in water, and in polar and apolar solvents, excluding fluorinated solvents, but including aromatic and chlorinated solvents. See Table II. The Fomblin HC fluids are both hydrophobic and lipophobic. In addition, the Fomblin HC fluids are Newtonian fluids and any emulsion containing these fluids are believed to become more Newtonian. Fomblin HC fluids are odorless, tasteless, colorless, non-greasy, non-volatile and transparent liquid polymers. The absence of hydrogen and the presence of strong covalent bonds, such as the carbon-oxygen bond and carbon-fluoride bond, insure excellent chemical and thermal stability. The ether bond in the molecule increases the conformational degree of freedom in the chain and permits polymers to be liquid even at very low temperatures. While Fomblin HC fluids have a very high concentration of organic fluoride, they are nevertheless free of fluoride and inorganic fluorides. Moreover, studies conducted by Ausimont, Milan, Italy, including acute toxicity tests in rats (by the oral route, interperitoneal route and the dermal route), suggest that the level of irritancy and toxicity is minimal. Still further, when injected into the skin, Fomblin HC fluids are completely inert. As a further advantage, Fomblin HC fluids are found to be non-irritating, according to CTFA Safety Testing Guidelines, and non-sensitizing in animal and human studies. Most importantly, Fomblin HC fluids have not shown evidence of mutagenicity during research studies at the Huntington Research Center in England.

In accomplishing the objectives of the present invention, the pharmaceutical compositions should be administered subcutaneously in effective amounts as micro-droplets at a desired site. It is currently believed that larger amounts can cause focal inflammations and drift. To administer micro-droplets, this can be accomplished simply through the use of a dental syringe armed with carpules of the augmenting pharmaceutical composition or neat liquids. The carpules should be of a special thick wall design, e.g., about 2 mm thick (not the standard carpule), to allow significant pressure to inject the pharmaceutical compositions or neat liquids through, for instance, a 27 or 30 gauge needle. Typical amounts of administration are about 0.005 ml to about 0.5 ml and preferably about 0.05 ml to about 0.2 ml and more preferably about 0.05 ml to about 0.1 ml. Of course, when the perfluoro-polyethers are formulated with other components, the amount administered will vary accordingly. Nonetheless, the amount of fluid in the carpule is self-limiting and will result in the administration of micro-droplets and will permit augmentation of small areas in one particular section.

EXAMPLE I

Guinea Pigs

Six male, hairless guinea pigs were used to augment dermal tissue. A dental syringe carpule was utilized to inject micro-injections of Fomblin HC/R and medical grade silicone in comparison studies. Six spots were picked on the back of the guinea pig for the subcutaneous injection of the Fomblin HC/R, along with six sites for the silicone. The amount per injection was 0.05 ml for both the Fomblin HC/R and silicone. Micro-droplet injections were placed and biopsies were taken of the resulting augmentation at one, three and six months.

Physiologically, the development of microencapsulization of the injected material encased in a mononuclear cell infiltrate, wrapping in a sheath of new formed collagen was demonstrated. This material was stable at one, three and six month time frames, as surveyed by histological examination. The inflammation had decreased during the three and six month periods, but the collagen had increased. There was no evidence of any migration into adjacent tissue and the animals stayed healthy.

EXAMPLE II

Humans

Forty patients with chronic ache vulgaris were chosen which had valley type scarring on the face, back or chest. They received the micro-droplet technique augmentation with the Fomblin HC/R at monthly intervals. The Fomblin HC/R was administered by subcutaneous injection. At each interval, each patient received several injections at different sites on an individual basis and the amount administered was between about 0.01 ml and about 0.05 ml per injection.

The average resultant augmentation of the tissue in the forty patients was about 85%. Patients were extremely pleased with their new appearance, without the valley shaped ache scars. Two of the patients developed inflammatory nodules at the injection site during one of the sessions however, these sites responded rapidly to intralesional steroid injection and disappeared.

These patients had other sessions of injections that also demonstrated no adverse reactions. It is believed that the episodes of inflammatory nodules were cases of macroinjections, instead of microinjections.

There was no evidence of allergic reactions and no evidence of migration of the augmentation material.

The present invention may, of course, be carried out in other specific ways than those herein set forth without departing from the spirit and essential characteristics of the invention. The present embodiments are, therefore, to be considered in all respects as illustrative and not restrictive and all changes coming within the scope of the appended claims.

Having described my invention, I claim:

1. A method for augmenting tissue, said method comprising:

injecting an effective tissue-augmenting amount of a perfluoropolyether compound to an individual in need thereof at a site of tissue loss or damage, whereby the tissue lost or damaged at that site is augmented.

2. The method of claim 1, wherein said perfluoropolyether compound is perfluoropolyethylisopropyl ether.

3. The method of claim 2, wherein said perfluoropolyethylisopropyl ether has an average molecular weight of 1,500 or 3,200.

4. The method of claim 1, wherein said perfluoropolyether compound is a perfluoropolyethylisopropyl ether having an average molecular weight of 6,250.

5. The method of claim 1, wherein said perfluoropolyether compound is administered as a pharmaceutical composition, said composition including a pharmaceutically acceptable vehicle.

6. The method of claim 5, wherein said pharmaceutical composition further comprises glycerin and sodium lauryl sulfate.

7. The method of claim 1, wherein said perfluoropolyether compound is administered as microdroplets.

8. The method of claim 1, wherein said injection is subcutaneous injection.

9. In combination, a syringe and perfluoropolyether compound for augmenting tissue, said syringe containing the perfluoropolyether compound.

10. The combination of claim 9, wherein said syringe includes a cartridge containing the perfluoropolyethor compound.

11. The combination of claim 10, wherein said cartridge contains about 0.2 ml to about 0.5 ml of said perfluoropolyether compound.

12. The combination of claim 9, wherein said syringe further includes a needle, said needle having a gauge of between about 27 and 30.

13. The combination of claim 9, wherein said perfluoropolyether compound is a perfluropolyethylisopropyl ether.

14. The combination of claim 13, wherein said perfluropolyethylisopropyl ether has an average molecular weight of 1,500 or 3,200.

15. The combination of claim 9, wherein said perfluoropolyether compound is a perfluoropolyethylisopropyl ether having an average molecular weight of 6,250.

16. The combination of claim 9, wherein said combination further includes glycerin, polypropylene glycol or sodium lauryl sulfate.

17. The combination of claim 9, wherein said combination further includes an additive selected from the group consisting of a steroid, antioxidant, preservative and emulsifier.

18. The combination of claim 10, wherein said cartridge has a side wall, said side wall having a thickness of about 2 mm.

* * * * *